April 30, 1963 E. E. WILLIAMS Plant Pat. 2,256
APRICOT TREE
Filed Oct. 27, 1960
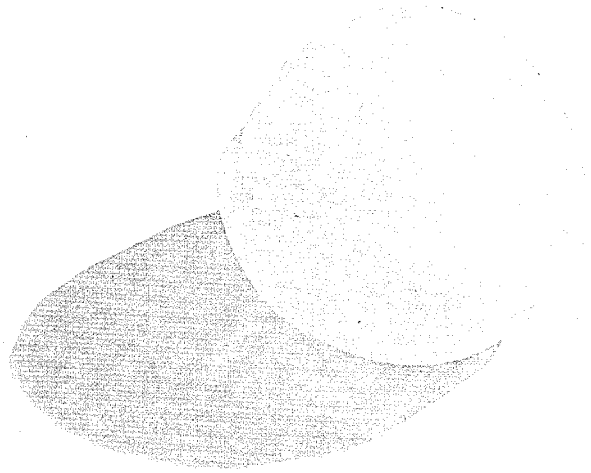

United States Patent Office

Plant Pat. 2,256
Patented Apr. 30, 1963

2,256
APRICOT TREE

Edgar E. Williams, Trinidad, Wash., assignor to Pacific Coast Nursery, Portland, Oreg., a firm doing business as a partnership Filed Oct. 27, 1960, Ser. No. 65,547
1 Claim. (Cl. 47—62)

The present invention relates to a new and distinct variety of apricot tree originating as a seedling of the variety of an apricot tree disclosed in my copending application, Serial Number 65,546, filed October 27, 1960. The new variety was discovered by me in a cultivated orchard on my property in Trinidad, Washington, approximately 13 years after the discovery of its parent on the same orchard property.

The direct parent of which present invention is a seedling, is a seedling of the variety known as Blenheim (unpatented). The direct variety, identified above by application number, is characterized by branches that spread slightly upright, while the present invention has limbs that spread laterally to a greater degree.

The new variety is substantially identical in all respects with its immediate parent, except that the leaves are slightly larger. The fruit is not characterized by toughness of skin which characterizes the parent. The fruit is more spherical. The blush more intense. The harvest date is approximately one week earlier and the fruit is firmer than the fruit of the parent tree.

Asexual reproduction of the new variety by grafting and budding in the Columbia River Basin in and adjacent Chelan County, Washington, establishes that the foregoing characteristics run true to form and are fixed and are transmitted through succeeding propagations.

The accompanying drawing shows a specimen of the fruit, in elevation.

The following is a detailed description of the new variety based upon observations of specimens grown in and adjacent Trinidad, Washington in the Columbia River Valley adjacent Chelan County, with color terminology in accordance with Nickerson Color Fan by Munsell Color Company as indicated, except where the general color terms of ordinary dictionary significance are obvious:

Dates of first picking: June 22, as compared to June 30 for immediate parent stock, and July 3 of Blenheim (unpatented) which was the parent stock for its immediate parent.

Tree: Very large, vigorous, upright, hardy, productive, regular bearing.

*Branches.*—Spread laterally.

*Leaves.*—Distinctive with finely serrated edge and the color is moderate olive-green slightly darker than color 7.5CY 4/4.

Flowers: Moderately pink, and having a blossom date about the same as Moorpark.

Fruit: Firm; 2 inches to 2⅜ inches in diameter; slightly ovate; halves are substantially equal with shallow suture; stem cavity is hollow; pit and pit cavity medium to large. Color—That half receiving the most sunlight is covered with a mottled diffused blush (7.5R 5/13), with undercolor 10YR 8/10.

Flesh: Firm and juicy.

Use: Market and dessert.

Keeping quality: Good.

I claim:

A new and distinct variety of apricot tree substantially as herein shown and described, characterized as to novelty by its similarity to its immediate parent variety and to its distant parent variety (Blenheim) but distinguished from both of said varieties by a bright reddish pink blush covering approximately 25% of the surface and a pinkish mottling over 50% of the surface and a strong reddish orange undercoat, having a harvesting date approximately one week earlier than its immediate parent and two weeks earlier than its distant parent Blenheim.

No references cited.